(12) United States Patent
Yao et al.

(10) Patent No.: US 9,533,479 B2
(45) Date of Patent: Jan. 3, 2017

(54) ABSORBENT ARTICLES HAVING ANTIMICROBIAL PROPERTIES AND METHODS OF MANUFACTURING THE SAME

(75) Inventors: Min Yao, Vernon Hills, IL (US); Daniel B. Love, Libertyville, IL (US); Amin Setoodeh, Kildeer, IL (US); Debashish Chakravarthy, Vernon Hills, IL (US)

(73) Assignee: Medline Industries, Inc., Mundelein, IL (US)

( * ) Notice: Subject to any disclaimer, the term of this patent is extended or adjusted under 35 U.S.C. 154(b) by 177 days.

(21) Appl. No.: 12/233,215

(22) Filed: Sep. 18, 2008

(65) Prior Publication Data

US 2010/0069861 A1 Mar. 18, 2010

(51) Int. Cl.
| | |
|---|---|
| *A61L 15/46* | (2006.01) |
| *A61F 13/511* | (2006.01) |
| *A61F 13/53* | (2006.01) |
| *B32B 33/00* | (2006.01) |
| *A61F 13/15* | (2006.01) |
| *A61F 13/84* | (2006.01) |

(52) U.S. Cl.
CPC ......... *B32B 33/00* (2013.01); *A61F 13/15804* (2013.01); *A61F 13/51113* (2013.01); *A61F 13/8405* (2013.01); *A61L 15/46* (2013.01); *A61F 2013/8414* (2013.01); *A61L 2300/206* (2013.01); *A61L 2300/404* (2013.01); *B32B 2307/7145* (2013.01); *B32B 2555/02* (2013.01)

(58) Field of Classification Search
CPC .................. A61F 13/8405; A61F 2013/5109; A61F 2013/5113; A61F 2013/8408; A61F 2013/8414; A61L 15/46

USPC ................................................. 604/359, 360
See application file for complete search history.

(56) References Cited

U.S. PATENT DOCUMENTS

| | | |
|---|---|---|
| 4,128,686 A | 12/1978 | Kyle et al. |
| 4,561,435 A | 12/1985 | McKnight et al. |
| 4,655,756 A | 4/1987 | Fawkes |
| 4,704,114 A | 11/1987 | Wilson et al. |
| 4,842,593 A | 6/1989 | Jordan et al. |
| 4,847,134 A | 7/1989 | Fahrenkrug et al. |
| 5,304,162 A | 4/1994 | Kuen |

(Continued)

FOREIGN PATENT DOCUMENTS

| | | |
|---|---|---|
| EP | 1 149 595 | 10/2001 |
| EP | 2 427 156 | 3/2012 |

(Continued)

OTHER PUBLICATIONS

Written Opinion corresponding to co-pending International Patent Application Serial No. PCT/US2009/057488, International Searching Authority; dated Nov. 23, 2009; 6 pages.

(Continued)

*Primary Examiner* — Lynne Anderson
*Assistant Examiner* — Kathryn E Ditmer
(74) *Attorney, Agent, or Firm* — Nixon Peabody LLP

(57) ABSTRACT

According to one embodiment, an absorbent article includes a moisture-impervious outer layer, an inner layer substantially co-extensive with the outer layer, and an absorbent layer interposed between the outer layer and the inner layer. The inner layer is treated with at least one antimicrobial booster. The absorbent layer is treated with at least one antimicrobial agent.

18 Claims, 2 Drawing Sheets

(56) References Cited

U.S. PATENT DOCUMENTS

| | | |
|---|---|---|
| 5,411,498 A | 5/1995 | Fahrenkrug et al. |
| 5,436,007 A | 7/1995 | Hartung et al. |
| 5,496,298 A | 3/1996 | Kuepper et al. |
| 5,527,302 A | 6/1996 | Endres et al. |
| 5,607,760 A | 3/1997 | Roe |
| 5,693,411 A | 12/1997 | Hansen et al. |
| 5,706,524 A | 1/1998 | Herrin et al. |
| 5,817,325 A | 10/1998 | Sawan et al. |
| 5,873,870 A | 2/1999 | Seitz et al. |
| 5,957,908 A | 9/1999 | Kline et al. |
| 5,993,840 A | 11/1999 | Fawkes et al. |
| 6,086,571 A | 7/2000 | Guevara et al. |
| 6,149,934 A | 11/2000 | Krzysik et al. |
| 6,153,209 A | 11/2000 | Vega et al. |
| 6,180,584 B1 | 1/2001 | Sawan et al. |
| 6,203,654 B1 | 3/2001 | McFall et al. |
| 6,217,890 B1 | 4/2001 | Paul et al. |
| 6,221,460 B1 | 4/2001 | Weber et al. |
| 6,225,524 B1 | 5/2001 | Guarracino et al. |
| 6,287,581 B1 | 9/2001 | Krzysik et al. |
| 6,290,924 B1 | 9/2001 | Chevallier |
| 6,296,862 B1 | 10/2001 | Paul et al. |
| 6,316,013 B1 | 11/2001 | Paul et al. |
| 6,352,528 B1 | 3/2002 | Weber et al. |
| 6,369,289 B1 | 4/2002 | Orr, III |
| 6,399,092 B1 | 6/2002 | Hobson et al. |
| 6,436,418 B1 | 8/2002 | Sheldon et al. |
| 6,475,197 B1 | 11/2002 | Krzysik et al. |
| 6,476,104 B1 | 11/2002 | Nakamura et al. |
| 6,482,422 B1 | 11/2002 | Paul et al. |
| 6,503,525 B1 | 1/2003 | Paul et al. |
| 6,503,526 B1 | 1/2003 | Krzysik et al. |
| 6,515,029 B1 | 2/2003 | Krzysik et al. |
| 6,534,074 B2 | 3/2003 | Krzysik et al. |
| 6,544,244 B1 | 4/2003 | Glaug et al. |
| 6,570,054 B1 | 5/2003 | Gatto et al. |
| 6,586,652 B1 | 7/2003 | Roe et al. |
| 6,592,702 B2 | 7/2003 | Nickell et al. |
| 6,613,955 B1 | 9/2003 | Lindsay et al. |
| 6,673,756 B2 | 1/2004 | Sonnenberg et al. |
| 6,689,932 B2 | 2/2004 | Kruchoski et al. |
| 6,703,536 B2 | 3/2004 | Roe et al. |
| 6,706,941 B2 | 3/2004 | Hisanaka et al. |
| 6,716,435 B1 | 4/2004 | Farmer et al. |
| 6,730,819 B1 | 5/2004 | Pesce |
| 6,749,860 B2 | 6/2004 | Tyrrell et al. |
| 6,756,520 B1 | 6/2004 | Krzysik et al. |
| 6,800,789 B2 | 10/2004 | Kasai et al. |
| 6,833,487 B2 | 12/2004 | Pesce et al. |
| 6,835,865 B2 | 12/2004 | Quincy, III |
| 6,844,430 B2 | 1/2005 | Pesce et al. |
| 6,855,134 B2 | 2/2005 | Brooks |
| 6,867,287 B2 | 3/2005 | Carlucci et al. |
| 6,887,564 B2 | 5/2005 | Gagliardini et al. |
| 6,905,488 B2 | 6/2005 | Olson |
| 6,960,702 B1 | 11/2005 | Kawakami et al. |
| 6,967,025 B2 | 11/2005 | Di Cintio et al. |
| 6,969,377 B2 | 11/2005 | Koele et al. |
| 7,025,974 B2 | 4/2006 | Farmer et al. |
| 7,045,673 B1 | 5/2006 | Batich et al. |
| 7,060,867 B2 | 6/2006 | Jameson |
| 7,217,804 B2 | 5/2007 | Pesce et al. |
| 7,265,257 B2 | 9/2007 | Baldwin et al. |
| 7,287,650 B2 | 10/2007 | Koslow |
| 7,291,370 B2 | 11/2007 | Gipson et al. |
| 7,655,828 B2 | 2/2010 | Rajagopalan |
| 2002/0106340 A1 | 8/2002 | Guskey |
| 2002/0128621 A1 | 9/2002 | Kruchoski et al. ...... 604/385.01 |
| 2002/0177828 A1 | 11/2002 | Batich et al. |
| 2003/0023216 A1 | 1/2003 | Carlucci et al. |
| 2003/0100879 A1 | 5/2003 | Kline et al. |
| 2003/0144638 A1 | 7/2003 | Quincy, III |
| 2004/0024104 A1 | 2/2004 | Ota et al. |
| 2004/0030315 A1 | 2/2004 | Brooks |
| 2004/0158216 A1 | 8/2004 | Kasai et al. |
| 2004/0191232 A1 | 9/2004 | Farmer et al. |
| 2004/0243076 A1 | 12/2004 | Husmark et al. |
| 2005/0003725 A1 | 1/2005 | Hill et al. |
| 2005/0033251 A1 | 2/2005 | Toreki et al. |
| 2005/0058683 A1 | 3/2005 | Levy et al. |
| 2005/0059941 A1 | 3/2005 | Baldwin et al. |
| 2005/0098759 A1* | 5/2005 | Frankenbach et al. ...... 252/8.91 |
| 2005/0101927 A1 | 5/2005 | Joseph et al. |
| 2005/0147655 A1 | 7/2005 | Bagwell et al. |
| 2005/0159719 A1 | 7/2005 | Kawakami et al. |
| 2005/0197641 A1 | 9/2005 | Rajagopalan |
| 2005/0222276 A1 | 10/2005 | Schmaus et al. |
| 2005/0249791 A1 | 11/2005 | Hobbs et al. |
| 2005/0271710 A1* | 12/2005 | Argo et al. ................... 424/443 |
| 2006/0025731 A1 | 2/2006 | Cohen |
| 2006/0089413 A1 | 4/2006 | Schmaus et al. |
| 2006/0160448 A1* | 7/2006 | Abraham ................ A61L 15/30 |
| | | 442/121 |
| 2006/0177429 A1 | 8/2006 | Farmer et al. |
| 2006/0286154 A1 | 12/2006 | Levy et al. |
| 2007/0032154 A1* | 2/2007 | Shanklin ........................ 442/123 |
| 2007/0048344 A1 | 3/2007 | Yahiaoui et al. |
| 2007/0048356 A1 | 3/2007 | Schorr et al. |
| 2007/0048358 A1 | 3/2007 | Schorr et al. |
| 2007/0054967 A1 | 3/2007 | Schmaus et al. |
| 2007/0059331 A1 | 3/2007 | Schmaus et al. |
| 2007/0077428 A1 | 4/2007 | Hamed et al. |
| 2007/0142798 A1 | 6/2007 | Goodlander et al. |
| 2007/0142804 A1 | 6/2007 | Bernard |
| 2007/0142806 A1 | 6/2007 | Roe et al. |
| 2007/0213412 A1 | 9/2007 | Bacon et al. |
| 2007/0219515 A1 | 9/2007 | Marsh et al. |
| 2007/0255192 A1* | 11/2007 | Patel et al. ....................... 602/48 |
| 2007/0265352 A1 | 11/2007 | Roeding et al. |
| 2007/0265590 A1 | 11/2007 | Sakaguchi |
| 2007/0298064 A1 | 12/2007 | Koslow |
| 2007/0298995 A1 | 12/2007 | Eggers et al. |
| 2008/0058738 A1 | 3/2008 | Roberts et al. |
| 2008/0058739 A1 | 3/2008 | Roberts et al. |
| 2008/0095719 A1 | 4/2008 | Herrmann et al. |
| 2008/0147027 A1 | 6/2008 | Sanabria et al. |
| 2008/0200890 A1 | 8/2008 | Wood et al. |
| 2009/0012487 A1 | 1/2009 | Park |
| 2009/0155325 A1 | 6/2009 | Wenzel et al. |
| 2009/0175806 A1 | 7/2009 | Modak et al. |
| 2010/0047303 A1 | 2/2010 | Yhlen et al. |
| 2010/0069861 A1 | 3/2010 | Yao et al. |

FOREIGN PATENT DOCUMENTS

| | | | |
|---|---|---|---|
| JP | 11310506 A * | 11/1999 | |
| JP | 11322591 A * | 11/1999 | |
| JP | 2003-081801 | 3/2003 | |
| WO | WO 9501151 A1 * | 1/1995 | ............... A61K 7/06 |
| WO | WO 2007/063065 | 6/2007 | |
| WO | WO2008157092 | 12/2008 | |
| WO | 2010-129227 | 11/2010 | |

OTHER PUBLICATIONS

International Search Report corresponding to co-pending International Patent Application Serial No. PCT/US2009/057488, International Searching Authority; dated Nov. 23, 2009; 2 pages.

*SymDiol 68 Synergistic Diol Blend*, Symrise, pp. 1-26 (available at least as early as Jun. 2008) (26 pages).

John P. Heggers et al., *Beneficial Effect of Aloe on Wound Healing in an Excisional Wound Model*, The Journal of Alternative and Complementary Medicine, vol. 2 (2), p. 271 (Abstract) (Jun. 1, 1996) (2 pages).

Phil Hindley, *Vantocil Cosmocil: Broad Spectrum and Fast-Acting Antimicrobials for the Professional and Consumer Hygiene Industries*, Arch, pp. 1-104 (Aug. 2007) (104 pages).

O.O. Agarry et al., *Comparative Antimicrobial Activities of Aloe Vera Gel and Leaf*, African Journal of Biotechnology, vol. 4 (12), pp. 1413-1414 (Dec. 2005) (2 pages).

(56) References Cited

OTHER PUBLICATIONS

Elizabeth F. Rostan M.D. et al., *Evidence Supporting Zinc as an Important Antioxidant for Skin*, International Journal of Dermatology, vol. 41, pp. 606-611 (2002) (6 pages).
*Remedy: Advanced Skin Care Products to Help Nourish the Skin*, Medline Industries, pp. 1-24 (Spring 2008) (24 pages).
International Search Report, Application PCT/US2010/032405 dated Dec. 21, 2010, 4 pages.
Written Opinion, Application PCT/US2010/032405 dated Dec. 21, 2010; 5 pages.
Extended European Search Report, European Patent Application No. 10772491.6, dated Mar. 6, 2014, 7 pages.
Extended European Search Report, European Patent Application No. 09815271.3, dated Aug. 5, 2015, 12 pages.

* cited by examiner

US 9,533,479 B2

ABSORBENT ARTICLES HAVING ANTIMICROBIAL PROPERTIES AND METHODS OF MANUFACTURING THE SAME

FIELD OF THE INVENTION

The present invention relates generally to an absorbent article and, in particular, to an absorbent article having antimicrobial properties.

BACKGROUND

Millions of Americans of all ages suffer from incontinence of the bowel or bladder. Whether an infant, adult, or elderly person, the underlying cause of incontinence varies but the method of treatment typically involves absorbent article products. Adult incontinent briefs, disposable diapers and underpads can alleviate some of the emotional and physical discomfort of incontinence by absorbing and containing liquid and other discharges from the human body to prevent body and clothing soiling.

However, the moisture-impervious layer that typically prevents absorbent articles from leaking also prevents air circulation, thus creating a warm, moist environment where bacteria and fungi can thrive. When fluids and discharge are introduced to the diaper, various bacteria from the wearer's digestive system are also present. Most bacteria are harmless or even beneficial to the wearer while in the digestive system; however, after urination or defecation, some bacteria (e.g., *Staphylococcus aureus* and *Streptococcus*) are dangerous microbial pathogens that can cause infectious diseases. Yet even benign bacteria can cause unpleasant odors or lead to urinary tract, bladder, or kidney infections. Moreover, prolonged exposure to urine and/or feces allows yeast-like fungi (e.g., *Candida albicans*) to develop and cause uncomfortable diaper rashes.

Accordingly, a need exists for absorbent articles that can prevent or inhibit the growth of microbes in or on absorbent articles.

BRIEF DESCRIPTION OF THE DRAWINGS

The foregoing and other advantages of the invention will become apparent upon reading the following detailed description and upon reference to the drawings.

Figure 1:
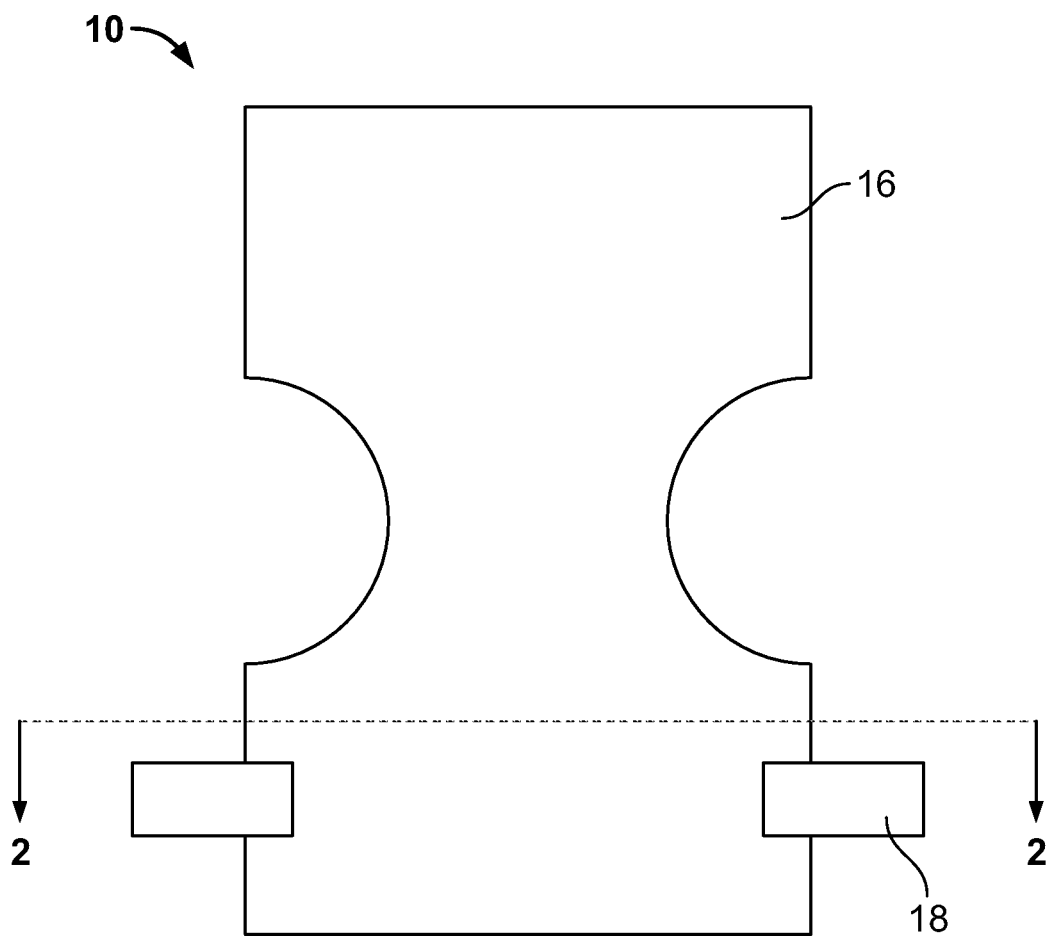
FIG. 1 illustrates a top view of an outer layer of a disposable diaper according to one embodiment.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Absorbent articles as described herein generally include a moisture-pervious inner layer, an absorbent layer, and a moisture-impervious outer layer. Although the remainder of the description will be specifically directed to a disposable diaper, it is to be understood that the embodiments may also be implemented on other absorbent articles such as, for example, adult incontinence briefs and underpads and that the properties and uses described below apply to these other absorbent articles as well.

Referring to FIG. 1, a top view of a disposable diaper 10 according to one embodiment is illustrated. The diaper 10 is of a substantially rectangular configuration; however, it is contemplated that any other suitable configuration may be employed. In this embodiment, the middle portion is contoured in an "hourglass" configuration to fit comfortably around a wearer's thighs when the diaper 10 is secured to the wearer.

Figure 2:
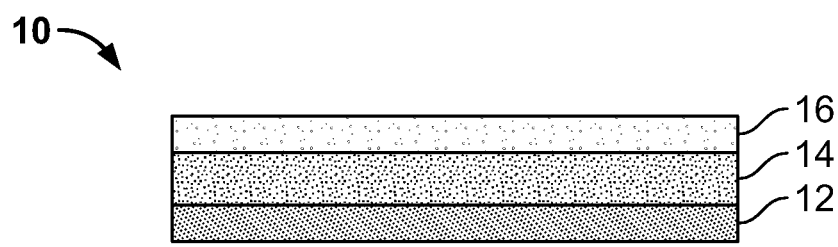
FIG. 2 illustrates a cross-section view generally taken through section line 2-2 of the diaper of FIG. 1.

The diaper 10 generally consists of several layers, as shown in FIG. 2. FIG. 2 is a cross-sectional view of the diaper 10 generally along section line 2-2 shown in FIG. 1. The diaper 10 includes an inner layer 12, an absorbent layer 14, and an outer layer 16. The inner layer 12 faces a wearer and contacts the skin of the wearer when the diaper 10 is secured to the wearer. The inner layer 12 can be composed of any moisture-pervious fabric suitable to allow bodily discharge to pass through the inner layer 12 and be absorbed by the absorbent layer 14. Non-limiting examples of materials suitable to form the inner layer 12 include polypropylene, polyethylene, polyester, materials having hydrophobic properties, combinations thereof and/or the like. Additionally, the inner layer 20 can be treated with a hydrophilic finish to improve pass through of liquids to diaper layers beneath the inner layer 20. Non-limiting examples of suitable hydrophilic finishes include anionic surfactants, cationic surfactants, nonionic surfactants, wetting agents (e.g., silicon based surfactants, glycol based surfactants), combinations thereof and/or the like. As will be discussed in greater detail below, the inner layer 12 is typically formed from a plastic resin of any of the above-referenced materials. This inner layer 12 is substantially co-extensive with the outer layer 16.

The absorbent layer 14 is positioned between the inner layer 12 and the outer layer 16. The absorbent layer 14 may be composed of any materials suitable for absorbing the fluids and discharge including, but not limited to, a fibrous material (e.g., fluffed wood pulp), a super absorbent polymer (SAP), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper 10 may vary depending upon whether it is intended for use by infants, children and/or adults.

The outer layer 16, which faces away from the wearer when the diaper 10 is secured to the wearer, is composed of a moisture-impervious fabric. Accordingly, the outer layer 16 may be made of any material suitable to minimize or prevent fluids and other discharge from escaping the diaper. Non-limiting examples of suitable materials for the outer layer 16 include polyethylene and/or breathable poly. According to some embodiments, the outer layer 12 can be a thin film such as, for example, polyethylene film. As will be discussed in greater detail below, the outer layer 16 is typically formed from a plastic resin of any of the above-referenced materials. This outer layer 16 that prevents diapers from leaking also prevents air circulation, thus creating a warm, moist environment where bacteria and fungi can thrive. This bacteria and fungi can cause infectious diseases, unpleasant odors, urinary tract infections, bladder infections, kidney infections, diaper rashes and the like.

The absorbent layer 14 is treated with at least one antimicrobial agent to prevent or substantially minimize the risk of these microbe-related effects by either killing or inhibiting the growth of microbes such as bacteria, microbial pathogens, fungi, and viruses. Not all antimicrobial agents can kill or inhibit the growth of all microbes. Rather, any one particular antimicrobial agent generally has a range of microbe types that the antimicrobial agent is effective against. As such, a variety of antimicrobial agents and/or combinations of antimicrobial agents may be applied to the absorbent layer 14 to provide protection against a broad range of microbes. Non-limiting examples of suitable antimicrobial agents for use in the embodiments described herein include cationic antimicrobial polymers (e.g., polyhexamethylene biguanide (PHMB)), mono- or poly-quaternary ammonium salt (QAS) based antimicrobials (e.g., trialkoxysilyl quaternary ammonium salt, 3-trimethoxy-silyl-propyldimethyloctadecyl ammonium chloride and its hydrolyzed product, polyquat-1), chlorinated phenoxy-based antimicrobials (e.g., triclosan), pyrithione based antimicrobials (e.g., zinc pyrithione), cationic polysaccharides (e.g., chitosan), aminopolysaccharides (e.g., chitin or chitosan derivatives), benzalkonium compounds (e.g., benzalkonium chloride, and a mixture of benzalkonium chloride, silver nitrate), nitro compounds (e.g., 5-nitrofurylacrolein), dimethylbenzylammonium chloride, chlorhexidines (e.g., chlorhexidine, chlorhexidine acetate, chlorhexidine gluconate, chlorhexidine hydrochloride), crosslinked polyethylene glycols and polyethylene glycols of differing molecular weights, hydantoin derivatives with halamine bond, antibiotics (e.g., polymycine, neomycin, kanamycin, grisofulvien), natural extracts with antimicrobial properties (e.g., grape fruit seed, hops, tea oil, aloe, thyme, rosemary, peppermint, basil, ginger), metallic materials in the form of metals (e.g., silver, copper, zinc materials and their oxides and salts), metal oxides (e.g., zinc oxide, silver oxide), metal salts (e.g., silver chloride, silver nitrate), metal complexes (e.g., silver-zinc zeolite), organo-metallics (e.g., tributylin maleate), combinations thereof or the like. Additional examples of suitable commercially avaliable antimicrobial agents are Haloshield® technology manufactured by Medline Inc., which is currently headquartered at One Medline Place, Mundelein, Ill. 60060 or HaloSource Inc., which is currently headquartered at 1631 220$^{th}$ Street SE, Bothell, Wash. 98021 and SilverClear® manufactured by Transtex Technologies, which is currently headquartered at 9600 Ignace St. Suite D, Brossard, Quebec, Canada J4Y2R4.

Generally, antimicrobial agents are classified as antibacterial agents (e.g., antibiotics, disinfectants, and antiseptics), antifungal agents, and antiviral agents depending upon the primary use of the particular agent. For example, if an antimicrobial agent is primarily used to target fungi, the antimicrobial agent may be referred to as an antifungal agent. However, it is to be understood that these classifications are non-limiting. For example, an antibacterial agent may be effective against fungi and an antifungal agent may be effective against bacteria. Therefore, it is to be understood that the absorbent layer 14 can be treated with any combination of antibacterial agent(s), antifungal agent(s), and/or antiviral agent(s).

Unfortunately, treating the absorbent layer 14 with certain antimicrobial agents can cause skin irritation for wearers. Skin irritation is an especially significant problem for wearers with sensitive skin or for wearers having a diaper rash. Skin irritation is often exacerbated by diaper-related substances such as colorant dyes.

To address the problems associated with skin irritation caused by the presence of antimicrobial agents, the inventors attempted to treat the inner layer 12, which contacts the wearer's skin, with at least one skin conditioner/moisturizer. Surprisingly, it was discovered that some skin conditioners/moisturizers enhance the antimicrobial effect of an antimicrobial agent through synergistic action when the skin conditioner/moisturizer mixes with the antimicrobial agent. Skin conditioners/moisturizers that interact synergistically with antimicrobial agents are hereinafter referred to as "preservative boosters." Non-limiting examples of commercially available preservative boosters include Symdiol-68®, Symdiol-68T®, Symclariol® and Hydrolite® manufactured by Symrise Inc., which is currently headquartered at 300 North Street, Teterboro, N.J. 07608. Symdiol 68® and Symdiol 68T® are generally classified as alkanediols and can be used alone or in combination in the present concepts. Specifically, Symdiol 68® includes 1,2-hexanediol and 1,2-octanediol, Symdiol 68T® includes 1,2-hexanediol, 1,2-octanediol and tropolone, Symclariol® includes 1,2-decanediol, and Hydrolite® includes 1,2-pentanediol. Other non-limiting examples of preservative boosters include aloe, alkyl diols, combinations thereof and/or the like.

Preservative boosters are a subset of a broader category of chemicals or substances called antimicrobial boosters that can be applied to the inner layer 12 of the diaper 10 to address the problem of skin irritation caused by the presence of antimicrobial agents. As used herein, an "antimicrobial booster" is any chemical or substance that increases the antimicrobial effect of an antimicrobial agent through synergistic action when mixed with the antimicrobial agent. A non-limiting example of an antimicrobial booster is ethylenediaminetetraacetic acid (EDTA). According to some embodiments, it is contemplated that the inner layer 12 can be treated with the antimicrobial booster(s) at a concentration level of 0.5%; however, any other suitable concentration may be utilized such as, for example, about 0.1% to about 5.0% concentration levels.

Prior to urination or defecation, the wearer is substantially insulated from the antimicrobial agent(s) present in the absorbent layer 14 because the absorbent layer 14 is disposed beneath the inner layer 12. As the inner layer 12 is the layer that contacts the wearer's skin, if the antimicrobial booster(s) is a preservative booster(s), the conditioning and moisturizing effects of the preservative booster(s) help maintain healthy skin and minimize any irritation or dryness that would otherwise result from diaper-related substances (e.g., colorant dyes) or trace amounts of antimicrobial agents that permeate from the absorbent layer 14 to the inner layer 12. Some antimicrobial boosters have inherent antimicrobial properties that provide minor protection against bacteria and fungi; however, a diaper treated with just an antimicrobial booster(s) would not have sufficient antimicrobial properties to adequately prevent or inhibit the growth of bacteria and/or fungi due to urine, feces, or other bodily discharge.

Urination, defecation, or release of other bodily discharges into the diaper 10 introduces moistures that permeate the inner layer 12 and absorb into the absorbent layer 14. The moistures mix with the antimicrobial booster(s) present in or on the inner layer 12 causing the antimicrobial booster(s) to also absorb into the absorbent layer 14 and synergistically combine with the antimicrobial agent(s). The synergistic action between the antimicrobial booster(s) and antimicrobial agent(s) enhances the antimicrobial effectiveness of the antimicrobial agent. Consequently, the combination of the antimicrobial booster(s) and the antimicrobial agent(s) acts faster and requires smaller concentrations or quantities to achieve a particular microbe kill rate than either the antimicrobial booster(s) or the antimicrobial agent(s) would individually.

There are several additional benefits to combining the antimicrobial booster(s) and antimicrobial agent(s) as described above. Because a smaller quantity of the antimicrobial agent(s) is needed to treat the absorbent layer 14, skin irritation due to the antimicrobial agent(s) is minimized. Skin irritation caused by antimicrobial agent(s) or other diaper related substances (e.g., colorant dyes) is further reduced by the skin conditioning and moisturizing properties of an antimicrobial booster(s) that is a preservative booster(s).

Reducing skin irritation not only increases the diaper wearer's comfort, it further permits a broader spectrum of antimicrobial agents to be utilized. Generally, diapers having an antimicrobial agent(s) but lacking an antimicrobial booster(s) are limited in the antimicrobial agents that can be used because some antimicrobial agents impermissibly irritate the wearer's skin. Because not all antimicrobial agents are effective against all microbes, a diaper limited to only inherently non-irritating antimicrobial agents may not be as effective against a targeted group of microbes as other antimicrobial agents. This problem may be exacerbated in the future because microbes continually develop resistances to commonly-used antimicrobial agents. A diaper including the synergistic combination of the antimicrobial booster(s) and antimicrobial agent(s) described herein can minimize the irritating effects of some antimicrobial agents previously considered unsuitable to a level that is permissible and, thus, broaden the spectrum of antimicrobial agents available. For example, the antimicrobial agent chlorhexidine is widely known to cause mild to moderate irritation when applied to the skin. For this reason, chlorhexidine is generally not considered for use an antimicrobial agent in diapers. Yet, surprisingly when chlorhexidine is combined with an antimicrobial booster, a smaller quantity or concentration of chlorhexidine is required and, thus, skin irritation from the presence of chlorhexidine can be minimized or reduced to an acceptable level such that this material can be used in diapers.

Incidentally, because the antimicrobial agent(s) can have a negative impact on the environment, reducing the quantity or concentration of the antimicrobial agent(s) in the diaper by using an antimicrobial booster also lessens the environmental impact of diapers discarded in landfills.

Figure 3:
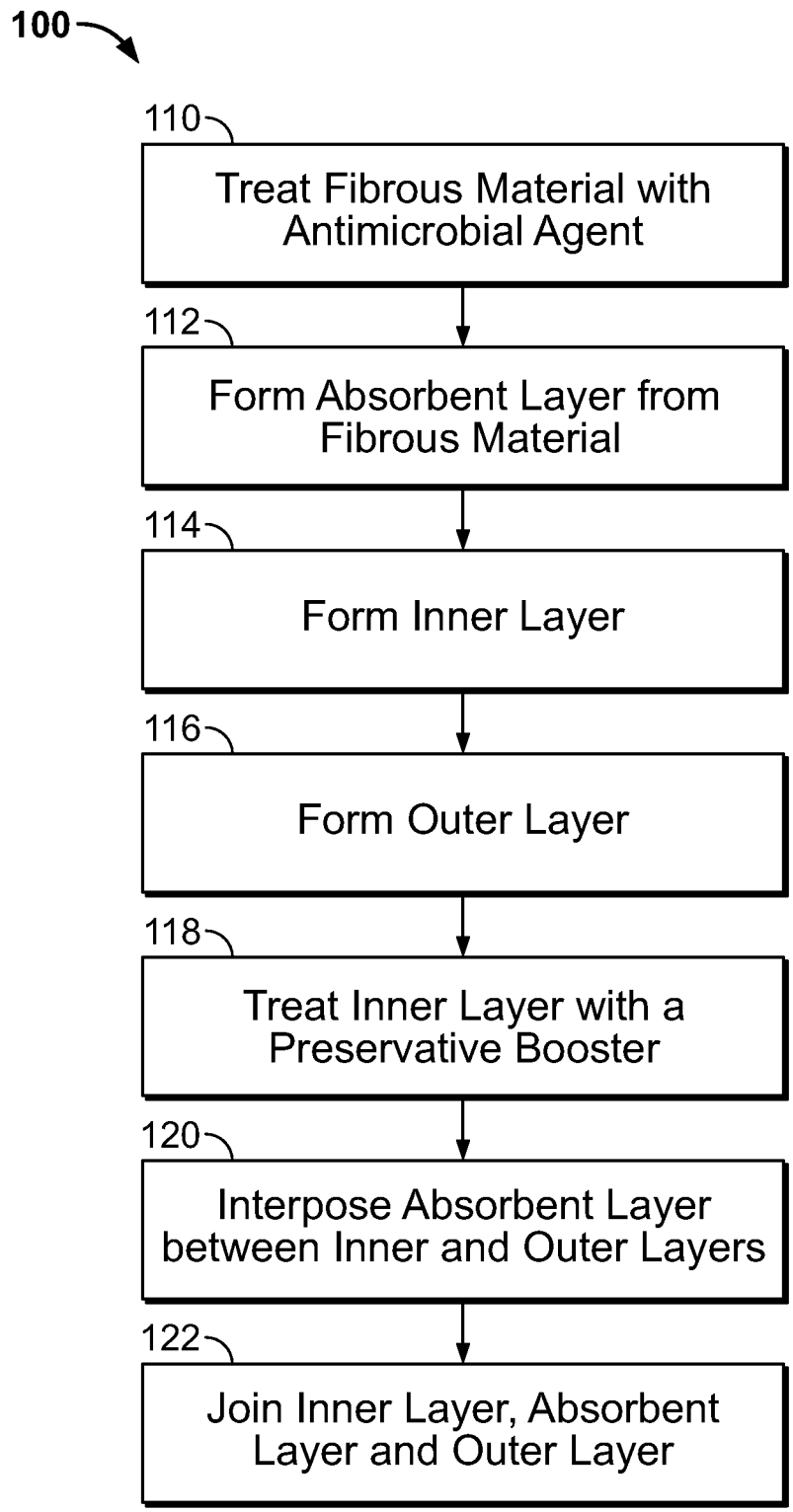
FIG. 3 illustrates an operational flow diagram for manufacturing a disposable diaper according to one embodiment.

Referring to FIG. 3, the operational flow of a method for manufacturing a disposable diaper 100 according to one of the embodiments described above is illustrated.

As disclosed above, the absorbent layer 14 can be formed from a combination of SAP and a fibrous material such as wood pulp. At block 110, the fibrous material is treated with at least one antimicrobial agent(s) by any process suitable to either absorb the antimicrobial agent(s) within or onto the fibers of the fibrous material (i.e., leaching) or covalently bond the antimicrobial agent(s) to the fibrous material (i.e., non-leaching). Depending upon the antimicrobial agent(s) selected, a binder may be required to facilitate bonding the antimicrobial agent(s) to the fibrous material and/or absorbing the antimicrobial agent(s) within or onto the fibrous material. Non-limiting examples of suitable binders include acetate, acrylate, acrylamide, urethane, vinyl, ester, other monomers, combinations thereof or the like. For example, the fibrous material can be dipped into or sprayed with a quantity of the antimicrobial agent(s).

At block 112, the absorbent layer 14 is formed from the SAP and the fibrous material by any suitable process. For example, the absorbent layer 14 can be formed on a conveyor belt passing under a series of pressurized nozzles. Depending upon the desired densities and distributions of SAP and fibrous material within the absorbent layer 14, a particular pressurized nozzle in the series of pressurized nozzles may spray SAP particles, fibrous material, or a mixture of SAP and fibrous material onto the conveyor surface. The bottom of the conveyor belt surface is perforated and a vacuum is applied from below so that the fibers are pulled down to form a long flat absorbent layer 14 as the materials are sprayed onto the conveyor belt. An absorbent layer 14 of uniform thickness can be achieved by a leveling roller used to remove a top portion of the SAP and/or fibrous material. According to alternative embodiments, it is contemplated that the absorbent layer 14 is composed of only the fibrous material by any suitable process such as the process described above.

At blocks 114 and 116, the inner layer 12 and the outer layer 16 are respectively formed by any dry laid or wet laid process. For example, the inner layer 12 and the outer layer 16 may be formed by a melt blown process, spunbond process, spunlace process, spunlaid process or the like. According to a melt blown process, a plastic resin (e.g., polypropylene or polyethylene) is melted and extruded though small holes by air pressure. The fibers condense onto a sheet as the air-blown stream of fibers cools. Heated rollers are then used to flatten the fibers and bond them together. The result is a "web" of nonwoven fabric, which can be rolled to form a bolt of fabric.

At block 118, the inner layer 12 is treated with at least one antimicrobial booster. The antimicrobial booster(s) can be applied to the inner layer 12 by any suitable process such as, for example, spraying, foaming (i.e., applying a foam containing the antimicrobial booster(s) to the inner layer 12), dipping, combinations thereof, or the like. According to an alternative embodiment, the antimicrobial booster(s) can be mixed with the plastic resin prior to forming the inner layer 12 at block 114.

At this point in the manufacturing process, an inner layer 12, an absorbent layer 14, and an outer layer 16 have been formed. At block 120, the absorbent layer 14 is interposed between the inner layer 12 and the outer layer 16 by, for example, feeding the absorbent layer 14 onto a conveyor with the outer layer 16 and then feeding the inner layer 12 into place above the absorbent layer 14. At block 122, the interposed layers are joined by a suitable means such as, for example, gluing, heating, ultrasonic welding, calendaring, combinations thereof or the like. The assembled layers are cut to a shape and size required for the particular absorbent article being manufactured.

It is contemplated that various additional features can be added to the diapers 10 at any point in the process described above. For example, one or more fasteners can be integrally formed with or attached to the inner layer 12, the outer layer 16, or both to secure the diaper 10 to the wearer. Referring back to FIG. 1, two fasteners 18 attached to the outer layer 16 are illustrated. It is contemplated that any suitable type of fasteners may be used such as, for example, adhesives, hook and loop mechanical fasteners, hook fasteners for attachment to the outer layer of the diaper, combinations thereof or the like. Additionally, elastic bands may be added to facilitate a snug fit or prevent leakage.

It will be appreciated by those skilled in the art that many of the steps for manufacturing the diaper 10 can be performed in a different order than that described above. For example, the absorbent layer 14, the inner layer 12, and the outer layer 16 can be formed in any order. Additionally, the inner layer 12, the absorbent layer 14, and the outer layer 16 can be cut into the shape of the absorbent article prior to interposing the layers or joining the layers. Although directly treating the SAP with the antimicrobial agent(s) causes the SAP to lose some of its absorption capacity, it is also contemplated that according to some embodiments, the absorbent layer 14 may be formed from the fibrous material and SAP first and then treated with the antimicrobial agent(s). Alternatively, a mixture of SAP and fibrous material can be treated with the antimicrobial agent(s) and then formed into the absorbent layer 14.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. An absorbent article comprising:
   a moisture-impervious outer layer;
   an inner layer substantially co-extensive with the outer layer, the inner layer being treated with at least one antimicrobial booster such that the at least one antimicrobial booster is mixed throughout the material of the inner layer prior to forming the inner layer, the at least one antimicrobial booster including two or more 1,2-alkanediols; and
   an absorbent layer interposed between the outer layer and the inner layer, the absorbent layer being treated with at least one antimicrobial agent such that a wearer is insulated from the at least one antimicrobial agent, the at least one antimicrobial agent comprising polyhexamethylene biguanide,
   wherein the at least one antimicrobial booster is configured to synergistically combine with the at least one antimicrobial agent when moisture is introduced into the article in use to (i) achieve a microbe kill rate that is greater than the microbe kill rate achieved by the antimicrobial booster or the antimicrobial agent individually, and (ii) minimize the irritating effects of the antimicrobial agent on a user when the absorbent article is in use.

2. The absorbent article of claim 1, wherein the at least one antimicrobial agent further comprises at least one of additional cationic antimicrobial polymers, mono-quaternary ammonium salt based antimicrobials, poly-quaternary ammonium salt based antimicrobials, chlorinated phenoxy-based antimicrobials, pyrithione based antimicrobials, cationic polysaccharides, aminopolysaccharides, benzalkonium compounds, nitro compounds, dimethylbenzylammonium chloride, chlorhexidines, cross-linked polyethylene glycols of differing molecular weights, polyethylene glycols of differing molecular weights, hydantoin derivatives with halamine bond, antibiotics, natural extracts with antimicrobial properties, metallic materials, and combinations thereof.

3. The absorbent article of claim 1, wherein the at least one antimicrobial agent further comprises at least one of trialkoxysilyl quaternary ammonium salt, 3-trimethoxy-silyl-propyldimethyloctadecyl ammonium chloride, polyquat-1, triclosan, zinc pyrithione, chitosan, chitosan derivatives, chitin derivatives, benzalkonium chloride, a mixture of benzalkonium chloride and silver nitrate, 5-nitrofurylacrolein, chlorhexidine, chlorhexidine acetate, chlorhexidine gluconate, chlorhexidine hydrochloride, polymycine, neomycin, kanamycin, grisofulvien, grape fruit seed, hops, tea oil, aloe, thyme, rosemary, peppermint, basil, ginger, silver, copper, zinc, zinc oxide, silver oxide, silver chloride, silver nitrate, silver-zinc zeolite, tributylin maleate, and combinations thereof.

4. The absorbent article of claim 1, wherein the two or more 1,2-alkanediols comprise 1,2-hexanediol and 1,2-octanediol.

5. The absorbent article of claim 1, wherein the at least one antimicrobial booster is a preservative booster.

6. The absorbent article of claim 1, wherein the at least one antimicrobial booster further includes at least one of aloe, alkyl diols, ethylenediaminetetraacetic acid, 1,2-hexanediol, 1,2-octanediol, tropolone, 1,2-decanediol, 1,2-pentanediol, and combinations thereof.

7. The absorbent article of claim 1, wherein the absorbent layer comprises a fibrous material.

8. The absorbent article of claim 1, wherein the absorbent article is a diaper, an underpad, or an adult incontinence brief.

9. The absorbent article of claim 1, wherein the inner layer is treated with the at least one antimicrobial booster at a concentration level of about 0.1% to about 5.0%.

10. The absorbent article of claim 9, wherein the inner layer is treated with the at least one antimicrobial booster at a concentration level of about 0.5%.

11. An absorbent article comprising:
    a moisture-impervious outer layer;
    an inner layer substantially co-extensive with the outer layer, the inner layer being treated with at least one antimicrobial booster such that the at least one antimicrobial booster is mixed throughout the material of the inner layer prior to forming the absorbent article, the at least one antimicrobial booster including one or more alkyl diol; and
    an absorbent layer interposed between the outer layer and the inner layer, the absorbent layer being treated with at least one antimicrobial agent such that a wearer is insulated from the at least one antimicrobial agent, the at least one antimicrobial agent comprising polyhexamethylene biguanide,
    wherein the at least one antimicrobial booster is configured to synergistically combine with the at least one antimicrobial agent when moisture is introduced into the article in use to (i) achieve a microbe kill rate that is greater than the microbe kill rate achieved by the antimicrobial booster or the antimicrobial agent individually, and (ii) minimize the irritating effects of the antimicrobial agent on a user when the absorbent article is in use.

12. The absorbent article of claim 11, wherein the at least one antimicrobial agent further comprises at least one of additional cationic antimicrobial polymers, mono-quaternary ammonium salt based antimicrobials, poly-quaternary ammonium salt based antimicrobials, chlorinated phenoxy-based antimicrobials, pyrithione based antimicrobials, cationic polysaccharides, aminopolysaccharides, benzalkonium compounds, nitro compounds, dimethylbenzylammonium chloride, chlorhexidines, cross-linked polyethylene glycols of differing molecular weights, polyethylene glycols of differing molecular weights, hydantoin derivatives with halamine bond, antibiotics, natural extracts with antimicrobial properties, metallic materials, and combinations thereof.

13. The absorbent article of claim 11, wherein the at least one antimicrobial agent further comprises at least one of trialkoxysilyl quaternary ammonium salt, 3-trimethoxy-silyl-propyldimethyloctadecyl ammonium chloride, polyquat-1, triclosan, zinc pyrithione, chitosan, chitosan derivatives, chitin derivatives, benzalkonium chloride, a mixture of benzalkonium chloride and silver nitrate, 5-nitrofurylacrolein, chlorhexidine, chlorhexidine acetate, chlorhexidine gluconate, chlorhexidine hydrochloride, polymycine, neomycin, kanamycin, grisofulvien, grape fruit seed, hops, tea oil, aloe, thyme, rosemary, peppermint, basil, ginger, silver, copper, zinc, zinc oxide, silver oxide, silver chloride, silver nitrate, silver-zinc zeolite, tributylin maleate, and combinations thereof.

14. The absorbent article of claim 11, wherein the at least one antimicrobial booster is a preservative booster.

15. The absorbent article of claim 11, wherein the absorbent layer comprises a fibrous material.

16. The absorbent article of claim 11, wherein the absorbent article is a diaper, an underpad, or an adult incontinence brief.

17. The absorbent article of claim 11, wherein the inner layer is treated with the at least one antimicrobial booster at a concentration level of about 0.1% to about 5.0%.

18. The absorbent article of claim 17, wherein the inner layer is treated with the at least one antimicrobial booster at a concentration level of about 0.5%.

* * * * *